(12) United States Patent
Ampolini et al.

(10) Patent No.: US 11,000,069 B2
(45) Date of Patent: May 11, 2021

(54) AEROSOL DELIVERY DEVICE AND METHODS OF FORMATION THEREOF

(71) Applicant: R.J. REYNOLDS TOBACCO COMPANY, Winston-Salem, NC (US)

(72) Inventors: Frederic Philippe Ampolini, Winston-Salem, NC (US); John DePiano, Burlington, MA (US); Matthew C. Ebbs, Newton-Highlands, MA (US); Frank S. Silveira, Wilmington, MA (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 1271 days.

(21) Appl. No.: 14/713,430

(22) Filed: May 15, 2015

(65) Prior Publication Data

US 2016/0331030 A1 Nov. 17, 2016

(51) Int. Cl.
*A24F 47/00* (2020.01)
*H05B 3/03* (2006.01)
(Continued)

(52) U.S. Cl.
CPC ......... *A24F 47/008* (2013.01); *A61M 11/042* (2014.02); *A61M 15/06* (2013.01); *H01M 10/48* (2013.01); *H01M 50/107* (2021.01); *H05B 3/03* (2013.01); *A61M 2016/003* (2013.01); *A61M 2016/0024* (2013.01);
(Continued)

(58) Field of Classification Search
None
See application file for complete search history.

(56) References Cited

U.S. PATENT DOCUMENTS

| 1,771,366 A | 7/1930 | Wyss et al. |
| 2,057,353 A | 10/1936 | Whittemore, Jr. |

(Continued)

FOREIGN PATENT DOCUMENTS

| AU | 276250 | 7/1965 |
| CA | 2 641 869 | 5/2010 |

(Continued)

OTHER PUBLICATIONS

"Define", Dictionary.com Unabridged. Random House, Inc. accessed at Dictionary.com on Mar. 12, 2018. (Year: 2018).*

*Primary Examiner* — Joseph S Del Sole
*Assistant Examiner* — Jamel M Nelson
(74) *Attorney, Agent, or Firm* — Womble Bond Dickinson (US) LLP

(57) ABSTRACT

The present disclosure relates to an aerosol delivery device including a shell that is divided into a first half and a second half along a longitudinal axis thereof. One or more batteries may be positioned within the shell along with a battery lead that provides an electrical connection to battery terminals. A base unit may be included and may have electrical contacts for matching with a battery terminal and the battery lead. The base unit can include one or both of a printed circuit board (PCB) and a pressure sensor. The shell can attach to a cartridge housing a reservoir for an aerosol-forming composition, a heater; a liquid transport element configured for transport of the aerosol forming composition between the reservoir and the heater; and heater terminals. Such construct can provide for simplified assembly of the device.

31 Claims, 8 Drawing Sheets

(51) Int. Cl.
*H01M 10/48* (2006.01)
*A61M 15/06* (2006.01)
*A61M 11/04* (2006.01)
*H01M 50/107* (2021.01)
*A61M 16/00* (2006.01)

(52) U.S. Cl.
CPC .............. *A61M 2016/0027* (2013.01); *A61M 2205/581* (2013.01); *A61M 2205/582* (2013.01); *A61M 2205/587* (2013.01); *A61M 2205/8206* (2013.01); *A61M 2207/00* (2013.01); *H01M 2220/30* (2013.01)

(56) References Cited

U.S. PATENT DOCUMENTS

| | | |
|---|---|---|
| 2,104,266 A | 1/1938 | McCormick |
| 3,200,819 A | 8/1965 | Gilbert |
| 4,284,089 A | 8/1981 | Ray |
| 4,303,083 A | 12/1981 | Burruss, Jr. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 9/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 7,117,867 B2 | 10/2006 | Cox et al. |
| 7,293,565 B2 | 11/2007 | Griffin et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 2002/0146242 A1 | 10/2002 | Vieira |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Hon |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2010/0319686 A1 | 12/2010 | Schennum |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0192619 A1 | 8/2013 | Tucker et al. |
| 2013/0199528 A1 | 8/2013 | Goodman et al. |
| 2013/0255702 A1 | 10/2013 | Griffith, Jr. et al. |
| 2013/0306084 A1 | 11/2013 | Flick |
| 2013/0319439 A1 | 12/2013 | Gorelick et al. |

(56) References Cited

U.S. PATENT DOCUMENTS

| | | |
|---|---|---|
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0345631 A1 | 11/2014 | Bowen et al. |
| 2015/0053217 A1 | 2/2015 | Steingraber et al. |

FOREIGN PATENT DOCUMENTS

| | | | |
|---|---|---|---|
| CN | 1541577 | 11/2004 | |
| CN | 2719043 | 8/2005 | |
| CN | 200997909 | 1/2008 | |
| CN | 101116542 | 2/2008 | |
| CN | 101176805 | 5/2008 | |
| CN | 201379072 | 1/2010 | |
| CN | 204015105 U | 12/2014 | |
| DE | 10 2006 004 4 | 8/2007 | |
| DE | 102006041042 | 3/2008 | |
| DE | 20 2009 010 400 | 11/2009 | |
| EP | 0 295 122 | 12/1988 | |
| EP | 0 430 566 | 6/1991 | |
| EP | 0 845 220 | 6/1998 | |
| EP | 1 618 803 | 1/2006 | |
| EP | 2 316 286 | 5/2011 | |
| EP | 2 835 063 | 2/2015 | |
| GB | 2469850 | 11/2010 | |
| WO | WO 1997/48293 | 12/1997 | |
| WO | WO 2003/034847 | 5/2003 | |
| WO | WO 2004/043175 | 5/2004 | |
| WO | WO 2004/080216 | 9/2004 | |
| WO | WO 2005/099494 | 10/2005 | |
| WO | WO 2007/078273 | 7/2007 | |
| WO | WO 2007/131449 | 11/2007 | |
| WO | WO 2009/105919 | 9/2009 | |
| WO | WO 2009/155734 | 12/2009 | |
| WO | WO 2010/003480 | 1/2010 | |
| WO | WO 2010/045670 | 4/2010 | |
| WO | WO 2010/073122 | 7/2010 | |
| WO | WO 2010/118644 | 10/2010 | |
| WO | WO 2010/140937 | 12/2010 | |
| WO | WO 2011/010334 | 1/2011 | |
| WO | WO 2012/072762 | 6/2012 | |
| WO | WO 2012/100523 | 8/2012 | |
| WO | WO 2013/089551 | 6/2013 | |
| WO | WO 2014/150979 | 9/2014 | |
| WO | WO 2015/003327 | 1/2015 | |
| WO | WO 2015/038981 | 3/2015 | |
| WO | WO 2015038981 A2 * | 3/2015 | ............ A24F 47/00 |
| WO | WO-2015038981 A3 * | 10/2015 | ............ G05B 15/02 |

* cited by examiner

AEROSOL DELIVERY DEVICE AND METHODS OF FORMATION THEREOF

FIELD OF THE DISCLOSURE

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from tobacco or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices, and heat generating sources set forth in the background art described in U.S. Pat. No. 7,726,320 to Robinson et al., U.S. Pat. Pub. No. 2013/0255702 to Griffith Jr. et al., and U.S. Pat. Pub. No. 2014/0096781 to Sears et al., which are incorporated herein by reference in their entirety. See also, for example, the various types of smoking articles, aerosol delivery devices, and electrically powered heat generating sources referenced by brand name and commercial source in U.S. patent application Ser. No. 14/170,838 to Bless et al., filed Feb. 3, 2014, which is incorporated herein by reference in its entirety.

It would be desirable to provide a reservoir for an aerosol precursor composition for use in an aerosol delivery device, the reservoir being provided so as to improve formation of the aerosol delivery device. It would also be desirable to provide aerosol delivery devices that are prepared utilizing such reservoirs.

SUMMARY OF THE DISCLOSURE

The present disclosure relates to aerosol delivery devices, methods of forming such devices, and elements of such devices. In some embodiments, the present disclosure relates to a power unit for an aerosol delivery device, the power unit being configured to provide for ease of manufacturing thereof and/or ease of recycling part or all of the elements used in forming the power unit. The power unit further may provide for lower capital expenditures and therefor enable formation of a lower cost aerosol delivery device suitable for being discarded in its entirety after use thereof. As such, the aerosol delivery device incorporating such power unit may be referred to as a low cost disposable device. The aerosol delivery device can be configured such that disposal may be carried out by recycling of the various elements thereof. For example, the connection of the power unit to a cartridge can be configured for easy disassembly. The shell of the power unit likewise can be configured for easy disassembly for removal of the elements contained therein. The various advantages of the power unit and the aerosol delivery device incorporating such power unit are further disclosed in the description of the various embodiments provided herein.

In some embodiments, the present disclosure particularly provides a power unit for an aerosol delivery device. The power unit can comprise an elongated shell having a proximal end and an opposing, distal end, the elongated shell being divided into two separate halves along a longitudinal axis thereof. A power unit according to the present disclosure may further described in relation to one or more of the following characteristics, which may be combined in any number without limitation.

The two halves of the elongated shell can be separably joined together.

The two halves of the elongated shell can be permanently joined together.

The two halves of the elongated shell can be welded together.

The power unit can comprise at least one elongated battery positioned within the elongated shell, the at least one elongated battery extending from the distal end of the elongated shell toward the proximal end of the elongated shell.

The power unit can comprise a battery lead including a projection that is configured for electrical connection with a terminal of the at least one battery and including an arm extending from the projection along the length of the at least one battery.

The power unit can comprise a base unit attached at the proximal end of the elongated shell.

The base unit can be attached to the at least one battery.

The base unit can comprise one or both of a printed circuit board (PCB) and a pressure sensor.

The base unit can include a first contact configured for electrical connection with the terminal of the at least one battery and can include a second contact configured for electrical connection with an opposing terminal of the at least one battery.

The battery lead projection can be configured for electrical connection with a negative terminal of the at least one battery, and the battery lead arm can be configured for electrical connection with one of the first contact and the second contact of the base unit.

The electrical connections in the power unit can be non-fused.

In some embodiments, the present disclosure can particularly provide a base unit that is configured for interconnecting a power unit and a cartridge to form an aerosol delivery device. The base unit can be configured for ease of assembly of the aerosol delivery device by providing "drop-in" connectivity between the power unit and the cartridge in relation to the electrical connections required therein. In particular, the present disclosure can provide a base unit for an aerosol delivery device, and the base unit can comprise a first section configured for engagement with a power unit and a second section configured for engagement with a cartridge, the base unit including a cavity extending at least partially therethrough. A base unit according to the present disclosure may further be described in relation to one or more of the following characteristics, which may be combined in any number without limitation.

The first section of the base unit can have a first diameter, and the second section of the base unit can have a second diameter that is less than the first diameter.

The first section of the base unit can be defined by a wall and a skirt extending longitudinally from the wall.

The skirt of the first section of the base unit can include at least one aperture, which may be characterized as an air intake.

The wall of the first section of the base unit can include a plurality of apertures, which may be characterized as heater terminal openings in that terminals extending from a heater in the cartridge may pass therethrough.

The second section of the base unit can be defined by a longitudinal wall extending from the wall of the first section of the base unit.

The cavity of the base unit can extend from the free end of the second section of the base unit entirely therethrough and extend at least partially into the first section of the base unit a sufficient distance to provide an air passage from the air intake on the skirt of the first section through at least a portion of the first section of the base unit and through the second section of the base unit.

The second section of the base unit can be sized and shaped to engage a flow tube in the cartridge.

The base unit can have a PCB positioned therein.

The base unit can have one or more contacts configured for electrical connection to one or more of a battery terminal, a battery lead, and a heater terminal.

One or more of the contacts can be positioned on the PCB.

One or more of the contacts can be positioned on the skirt of the first section of the base unit.

The base unit can include one or more clips configured for attaching the base unit to a battery in the power unit.

The first section of the base unit can comprise a support plate positioned therein.

The support plate can be positioned between the air intake and the distal end of the first section of the base unit.

The PCB can be attached to the support plate.

The support plate can provide a liquid impermeable barrier.

Further to the foregoing, the present disclosure also can provide an aerosol delivery device that includes one or both of a power unit and base unit as described above and as described throughout the present disclosure. In some embodiments, an aerosol delivery device can comprise: a first elongated shell configured for housing an aerosol-forming composition and having a mouth end and an opposing joining end; and a second elongated shell having a proximal end configured for connection with the joining end of the first elongated shell and having an opposing, distal end, the second elongated shell being divided into two separate halves along a longitudinal axis thereof. An aerosol delivery device according to the present disclosure may further be described in relation to one or more of the following characteristics, which may be combined in any number without limitation.

The two halves of the second elongated shell can be separably joined together.

The two halves of the second elongated shell can be permanently joined together.

The two halves of the second elongated shell can be welded together.

The second elongated shell can comprise at least one elongated battery positioned therein, the at least one elongated battery extending from the distal end of the second elongated shell toward the proximal end of the second elongated shell.

The aerosol delivery device can comprise a base unit configured for connection with the first elongated shell and the second elongated shell. The base unit may be defined according to any embodiments described herein, separably or in combination.

The base unit can comprise one or both of a printed circuit board (PCB) and a pressure sensor.

The base unit can include a first contact configured for electrical connection with a terminal of the at least one battery and can include a second contact configured for electrical connection with an opposing terminal of the at least one battery.

The aerosol delivery device can comprise a battery lead including a projection that is configured for electrical connection with the opposing terminal of the at least one battery and including an arm extending from the projection along the length of the at least one battery so as to be in electrical connection with the second contact of the base unit.

The electrical connections in the aerosol delivery device can be non-fused.

The can comprise an elongated flow tube positioned at least partially within the first elongated shell, the elongated flow tube comprising a central airflow passage therethrough.

The elongated flow tube can be configured for one or both of physical and electrical connection with the base unit.

The elongated flow tube can comprise a plurality of heater terminals configured for electrical connection with the base unit.

The aerosol delivery device can comprise a heater positioned within the first elongated shell.

The aerosol delivery device can comprise a reservoir positioned within the first shell and configured for storing the aerosol-forming composition.

The aerosol delivery device can comprise a liquid transport element configured for transfer of the aerosol-forming composition from the reservoir to the heater.

The aerosol delivery device can comprise a mouthpiece attached to the mouth end of the first elongated shell.

In some embodiments, an aerosol delivery device can comprise: a first elongated shell having a mouth end and an opposing joining end, the first elongated shell housing: a reservoir for an aerosol-forming composition: a heater; a liquid transport element configured for transport of the aerosol forming composition between the reservoir and the heater; and heater terminals. The aerosol delivery further can comprise a second elongated shell having a proximal end configured for connection with the joining end of the first elongated shell and having an opposing, distal end, the second elongated shell being divided into two separate halves along a longitudinal axis thereof; at least one battery positioned within the second elongated shell; a base unit comprising: one or both of a printed circuit board (PCB) and a pressure sensor; a first contact configured for electrical connection with a terminal of the at least one battery; and a second contact configured for electrical connection with an opposing terminal of the at least one battery. The base unit particularly can be in electrical connection with the heater terminals. An aerosol delivery device according to the present disclosure may further be described in relation to one or more of the following characteristics, which may be combined in any number without limitation.

The aerosol delivery device can comprise a battery lead including a projection that is configured for electrical connection with the opposing terminal of the at least one battery and including an arm extending from the projection along the length of the at least one battery so as to be in electrical connection with the second contact of the base unit.

The aerosol delivery device can comprise an elongated flow tube positioned at least partially within the first elongated shell, the elongated flow tube comprising a central airflow passage therethrough.

The heater terminals can pass through the flow tube. The heater terminals particularly can pass through a flange portion of the flow tube.

The flow tube can be attached to the base unit.

The joining end of the first elongated shell can be connected to at least a portion of the base unit.

The proximal end of the second elongated shell can be connected to at least a portion of the base unit.

In some embodiments, the present disclosure further can provide methods for forming an aerosol delivery device. As described herein, the methods can be characterized in relation to the ease of combining the many elements of the aerosol delivery device and the ability to simply dissemble the device for recycling one or more components thereof. In some embodiments, a method for forming an aerosol delivery device can comprise: providing a first longitudinal half shell that is configured for attachment to a second longitudinal half shell to form an elongated clam shell that is divided into a first half and a second half along a longitudinal axis thereof; placing a battery lead and at least one battery into the first longitudinal half shell such that a projection of the battery lead is in electrical connection with a first terminal of the at least one battery and such that an arm of the battery lead extends from the projection along the length of the at least one battery; providing a base unit comprising one or both of a printed circuit board (PCB) and a pressure sensor, and further comprising a first contact configured for electrical connection with a second terminal of the at least one battery and a second contact configured for electrical connection with the arm of the battery lead; providing a cartridge comprising a shell housing: a reservoir for an aerosol-forming composition: a heater; a liquid transport element configured for transport of the aerosol forming composition between the reservoir and the heater; and heater terminals; combining the cartridge, the base unit, and the first longitudinal half shell such that the heater terminals are in electrical connection with the base unit, the first contact of the base unit is in electrical connection with the second terminal of the at least one battery, and the second contact of the base unit is in electrical connection with the arm of the battery lead; and pairing the second longitudinal half shell to the first longitudinal half shell. A method of forming an aerosol delivery device according to the present disclosure may further be described in relation to one or more of the following characteristics, which may be combined in any number without limitation.

The method can comprise first adding the base unit to the first longitudinal half shell and then attaching the cartridge to the base unit.

The method can comprise first attaching the cartridge to the base unit and then adding the base unit to the first longitudinal half shell.

The method can comprise one or more of crimping, welding (e.g., laser welding or ultrasonic welding), and gluing the clam shell to one or both of the base unit and the cartridge shell.

The method can comprise adding a label to the aerosol delivery device. For example, a suitably sized sheet of paper or similar material commonly used for forming a wrapper or label may be positioned around the aerosol delivery device. The label may completely or partially surround the aerosol delivery device circumferentially. The label may completely or partially cover the union (or connection point) between the base unit and the cartridge and may extend substantially from the distal end of the base unit to the mouthpiece on the cartridge. The label may adhere to one or both of the base unit and the cartridge. The presence of the label and its attachment to the base unit and the cartridge may function to secure the cartridge to the base unit. The presence of the label may replace or supplement one or more further methods described herein for attaching the base unit and the cartridge.

BRIEF DESCRIPTION OF THE FIGURES

Figure 1:
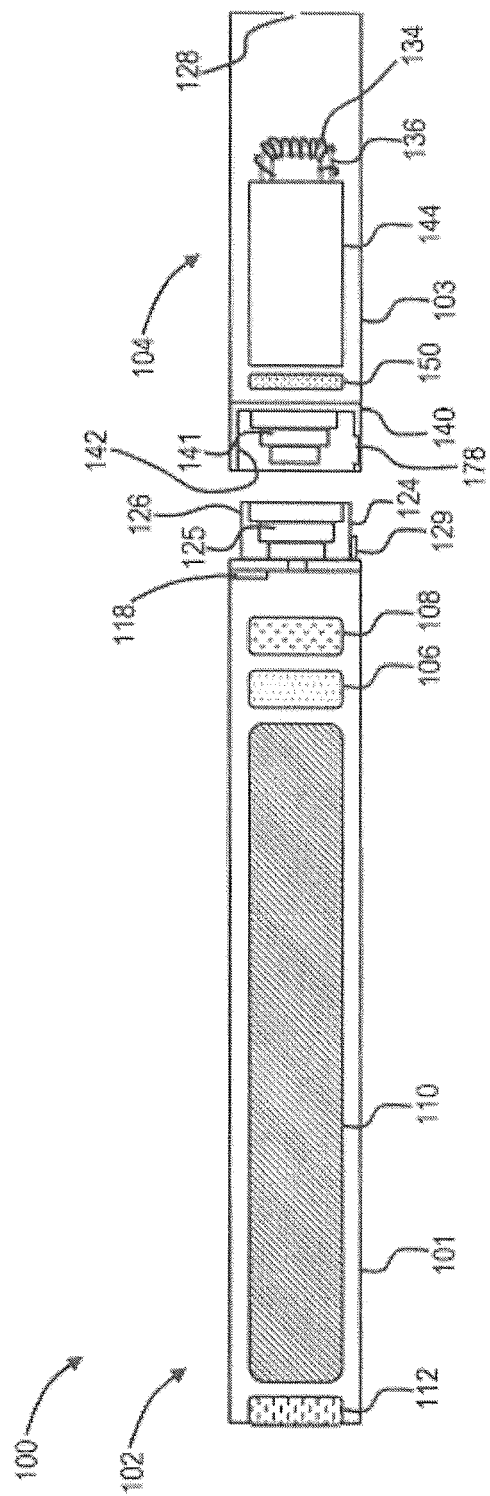
Figure 2:
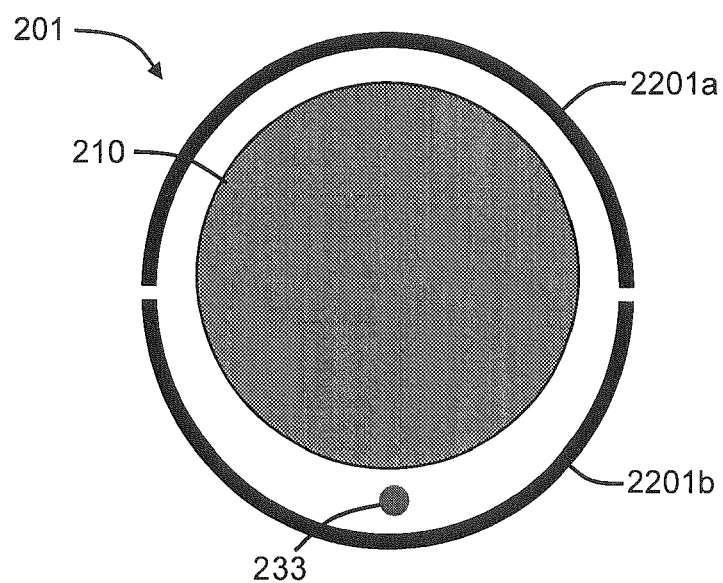
Figure 3:
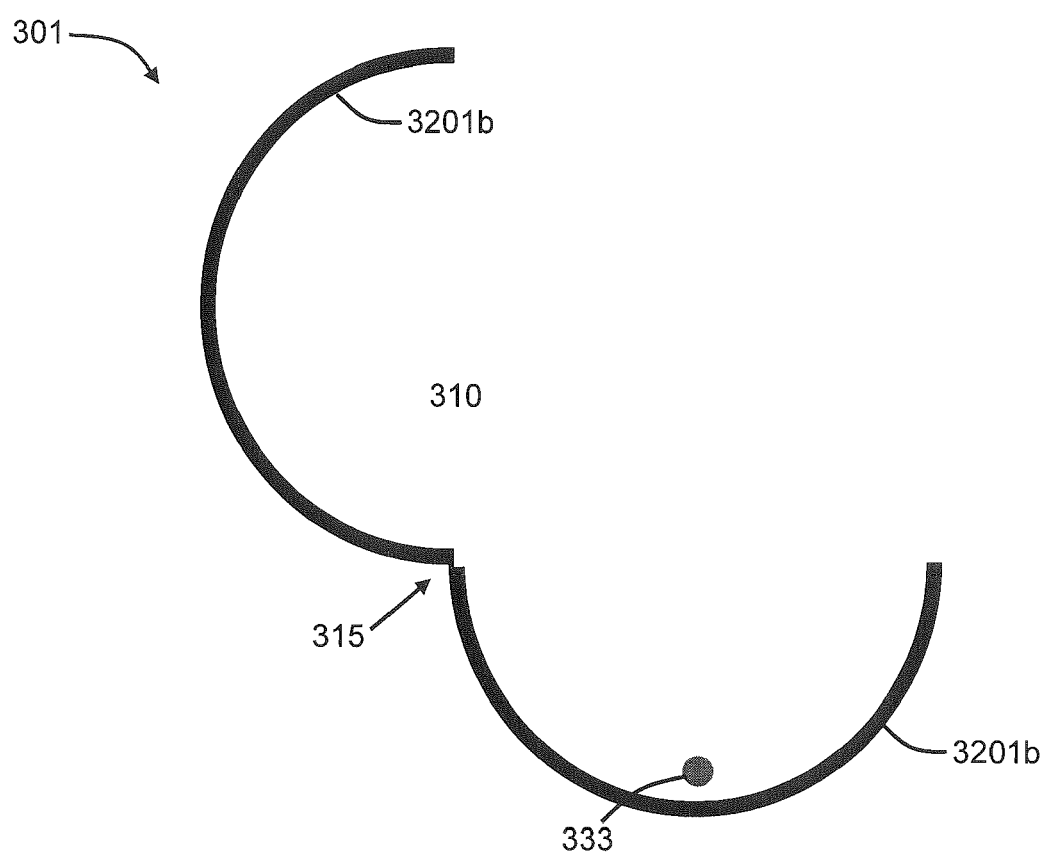
Figure 4:
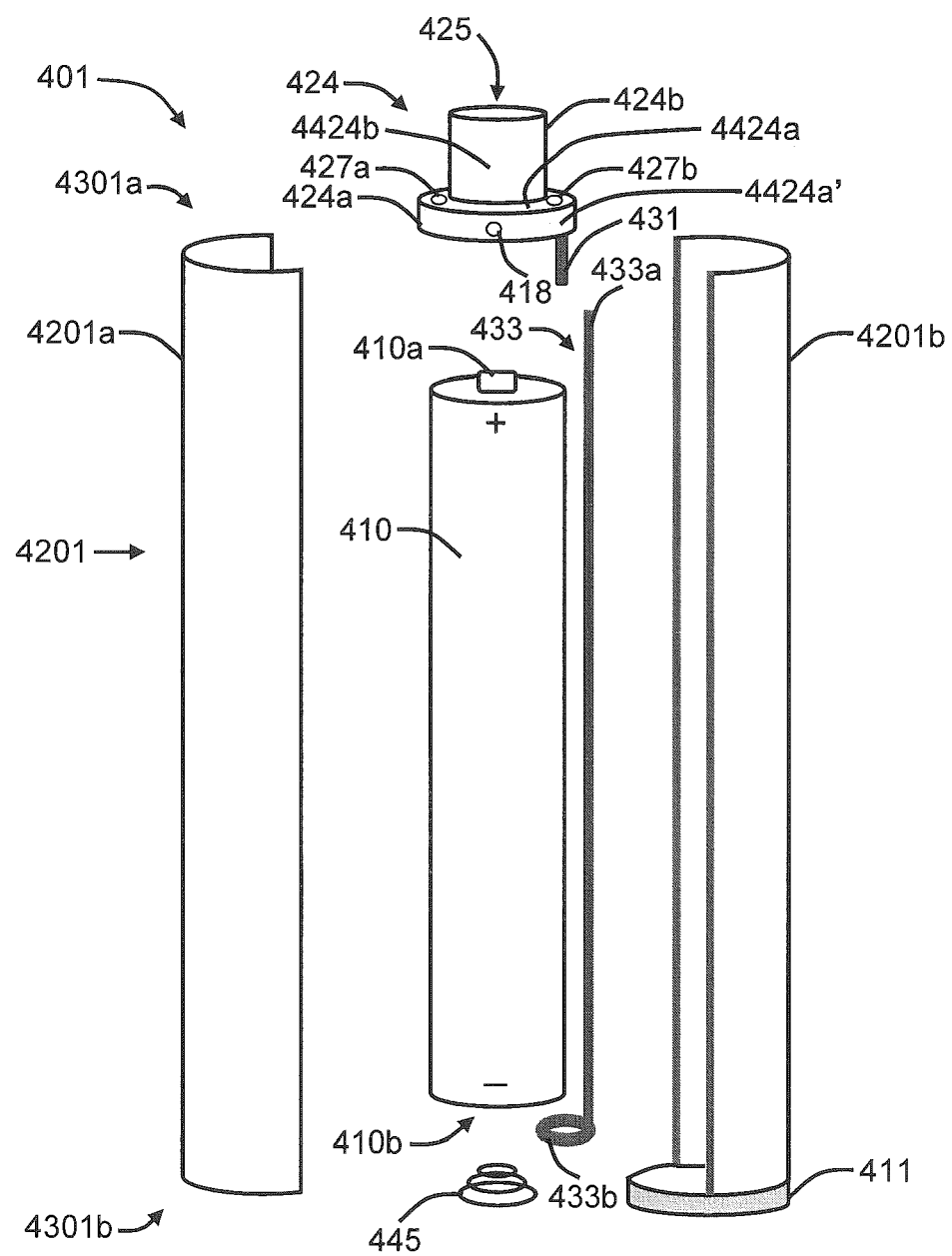
Figure 5A:
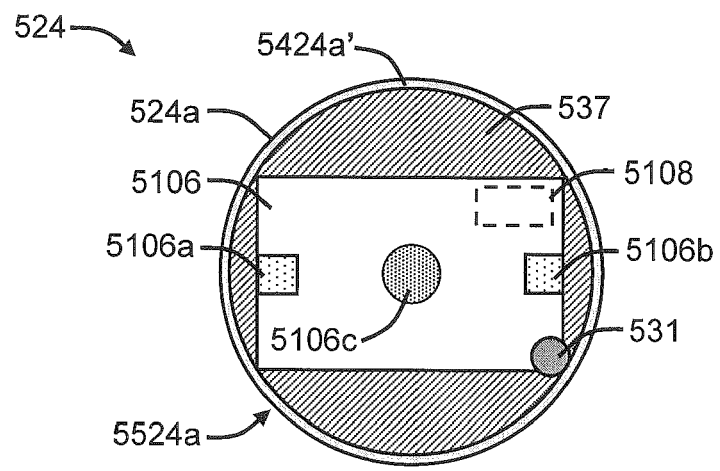
Figure 5B:
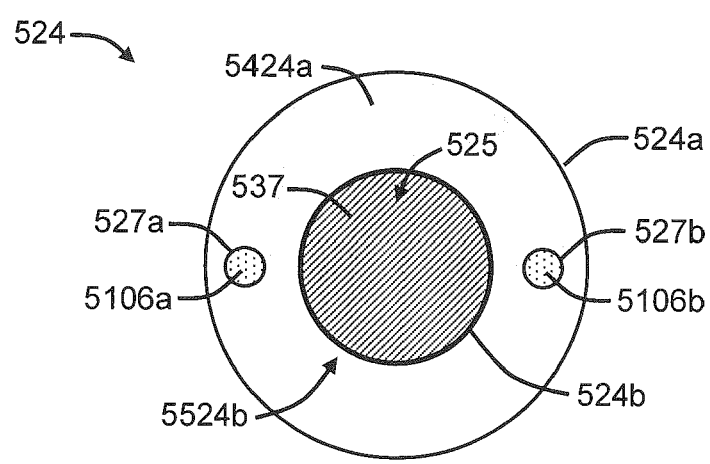
Figure 6:
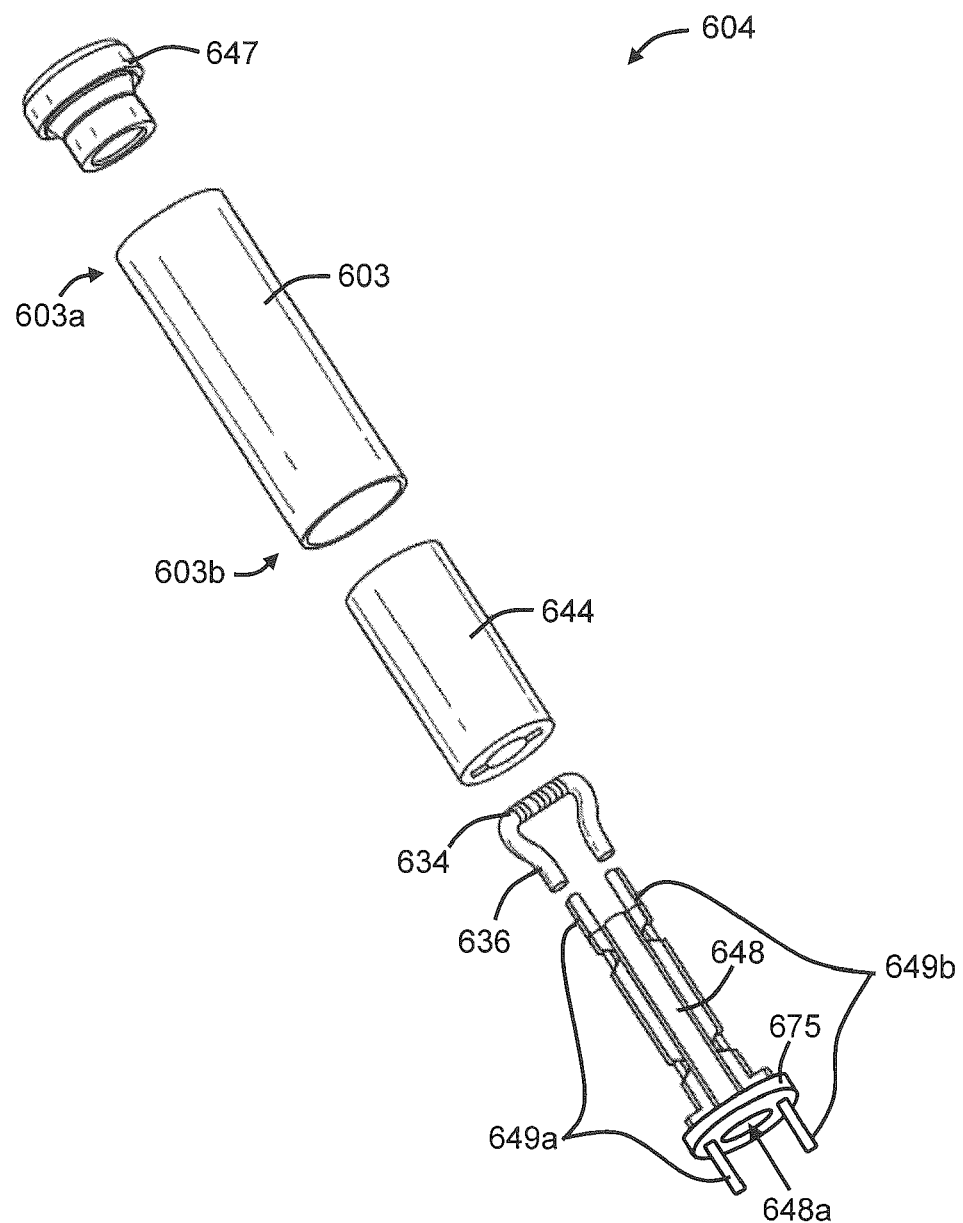
Figure 7A:
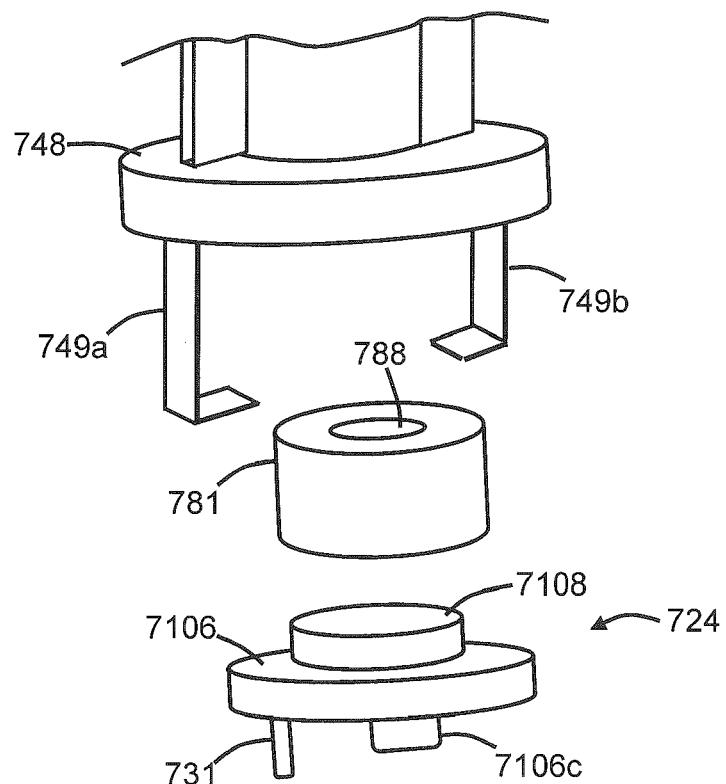
Figure 7B:
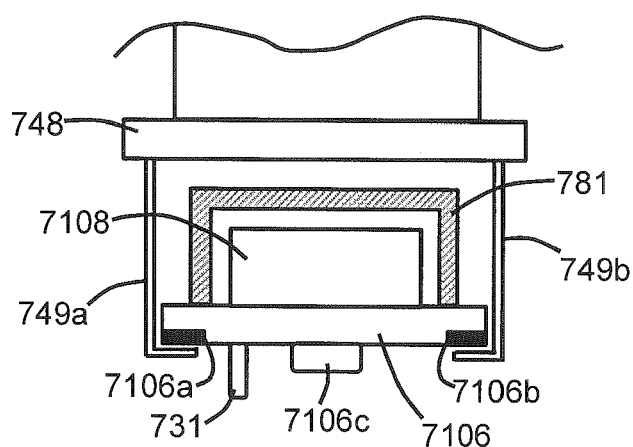
Figure 8A:
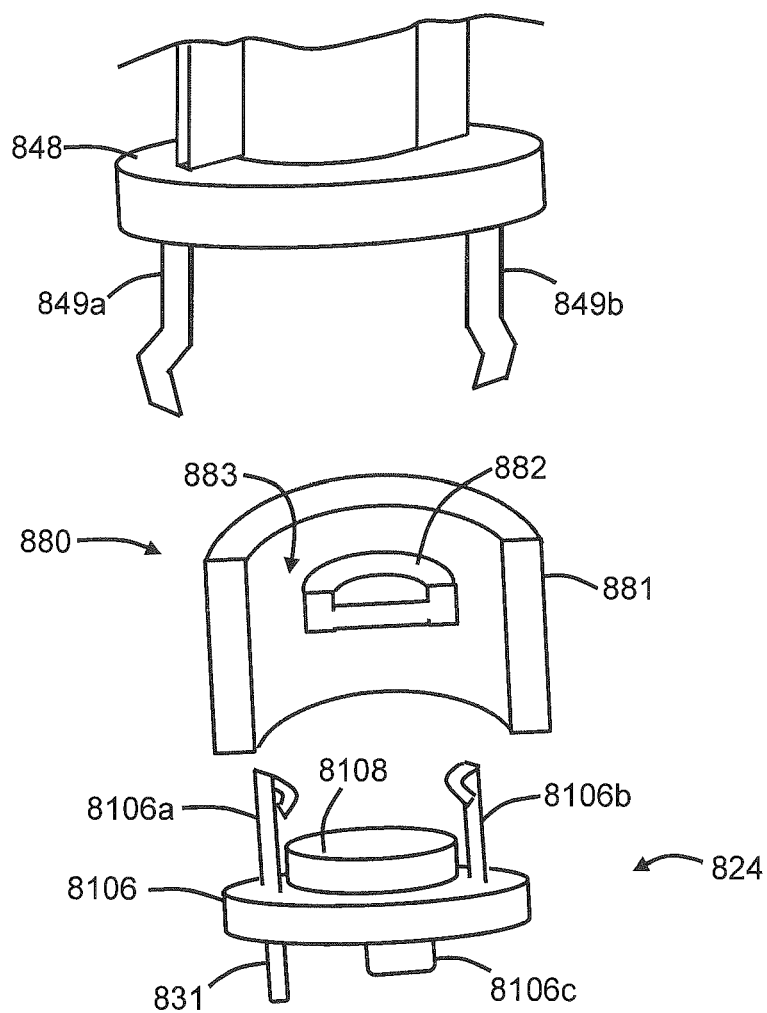
Figure 8B:
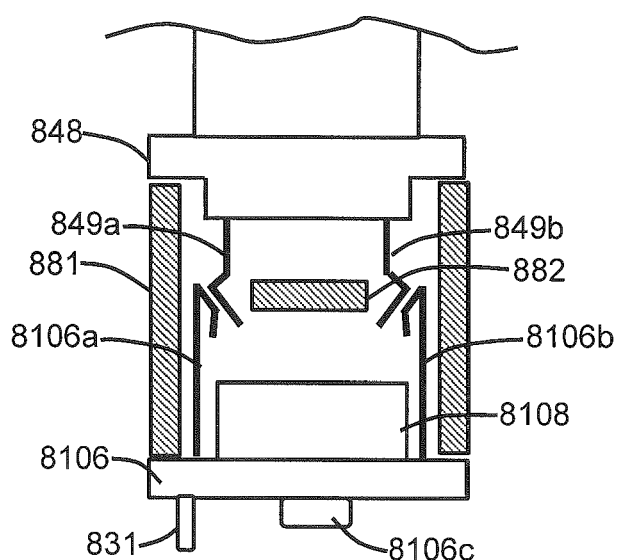

Having thus described the disclosure in the foregoing general terms, reference will now be made to the accompanying drawings, which are not necessarily drawn to scale, and wherein:

FIG. 1 is a partially cut-away view of an aerosol delivery device comprising a cartridge and a control body including a variety of elements that may be utilized in an aerosol delivery device according to various embodiments of the present disclosure;

FIG. 2 is a cross-section of a power unit according to an exemplary embodiment of the present disclosure illustrating the relationship of a battery and a battery lead to the two halves of a clam shell, wherein the halves of the claim shell are combined;

FIG. 3 is a cross-section of a power unit according to an exemplary embodiment of the present disclosure illustrating the relationship of a battery and a battery lead to the two halves of a clam shell, wherein the clam shell is in an open configuration;

FIG. 4 is an exploded view of a power unit according to an exemplary embodiment of the present disclosure, wherein the power unit includes an associated base unit according to an exemplary embodiment of the present disclosure;

FIG. 5a is a plan view of the distal end of a base unit according to an exemplary embodiment of the present disclosure;

FIG. 5b is a plan view of the proximal end of the base unit according to an exemplary embodiment of the present disclosure;

FIG. 6 is an exploded view of a cartridge useful for combination with a power unit and/or a base unit according to an exemplary embodiment of the present disclosure;

FIG. 7a is an exploded view of a partial flow tube, a base unit, and an insulator cap according to an exemplary embodiment of the present disclosure illustrating a functional relationship therebetween;

FIG. 7b is a cross-section of a partial flow tube, a base unit, and an insulator cap according to an exemplary embodiment of the present disclosure illustrating a substantially permanent engagement thereof;

FIG. 8a is an exploded view of a partial flow tube, a base unit, and a middle housing according to an exemplary embodiment of the present disclosure illustrating a functional relationship therebetween; and FIG. 8b is a cross-section of a partial flow tube, a base unit, and a middle housing according to an exemplary embodiment of the present disclosure illustrating a removable engagement thereof.

DETAILED DESCRIPTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As described hereinafter, embodiments of the present disclosure relate to aerosol delivery systems. Aerosol delivery systems according to the present disclosure use electrical energy to heat a material (preferably without combusting the material to any significant degree and/or without significant chemical alteration of the material) to form an inhalable substance; and components of such systems have the form of articles that most preferably are sufficiently compact to be considered hand-held devices. That is, use of components of preferred aerosol delivery systems does not result in the production of smoke—i.e., from by-products of combustion or pyrolysis of tobacco, but rather, use of those preferred systems results in the production of vapors resulting from volatilization or vaporization of certain components incorporated therein. In preferred embodiments, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery systems of the present disclosure generally include a number of components provided within an outer body or shell, which may be referred to as a housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing, or the elongated housing can be formed of two or more separable bodies. For example, an aerosol delivery device can comprise an elongated shell or body that can be substantially tubular in shape and, as such, resemble the shape of a conventional cigarette or cigar. In one embodiment, all of the components of the aerosol delivery device are contained within one housing. Alternatively, an aerosol delivery device can comprise two or more housings that are joined and are separable. For example, an aerosol delivery device can possess at one end a control body comprising a housing containing one or more power and/or control components (e.g., a battery and various electronics for controlling the operation of that article), and at the other end and removably attached thereto an outer body or shell containing aerosol-forming components (e.g., a heater and a reservoir storing an aerosol precursor composition).

Aerosol delivery systems of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microcontroller or microprocessor), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

In various embodiments, an aerosol delivery device can comprise a reservoir configured to retain the aerosol precursor composition, which also may be referred to as an aerosol forming composition. The reservoir particularly can be formed of a porous material (e.g., a fibrous material) and thus may be referred to as a porous substrate (e.g., a fibrous substrate).

A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a continuous glass fiber material or polyethylene terephthalate. In particular embodiments, a cellulose acetate material can be used. In other exemplary embodiments, a carbon material can be used. A reservoir may be substantially in the form of a container and may include a fibrous material included therein.

One example embodiment of an aerosol delivery device 100 according to the present disclosure is provided in FIG. 1. As seen in the cut-away view illustrated therein, the aerosol delivery device 100 can comprise a control body 102 and a cartridge 104 that can be permanently or detachably aligned in a functioning relationship. Engagement of the control body 102 and the cartridge 104 can be snap fit (as illustrated), threaded, interference fit, magnetic, or the like. In particular, connection components, such as further described herein may be used. For example, the control body may include a coupler that is adapted to engage a connector on the cartridge.

In specific embodiments, one or both of the control body 102 and the cartridge 104 may be referred to as being disposable or as being reusable. For example, the control body may have a replaceable battery or a rechargeable battery and thus may be combined with any type of recharging technology, including connection to a typical electrical outlet, connection to a car charger (i.e., cigarette lighter receptacle), and connection to a computer, such as through a universal serial bus (USB) cable. For example, an adaptor including a USB connector at one end and a control body connector at an opposing end is disclosed in U.S. Pat. Pub. No. 2014/0261495 to Novak et al., which is incorporated herein by reference in its entirety. Further, in some embodiments the cartridge may comprise a single-use cartridge, as disclosed in U.S. Pat. No. 8,910,639 to Chang et al., which is incorporated herein by reference in its entirety.

As illustrated in FIG. 1, a control body 102 can be formed of a control body shell 101 that can include a control component 106 (e.g., a printed circuit board (PCB), an integrated circuit, a memory component, a microcontroller, or the like), a flow sensor 108, a battery 110, and an LED 112, and such components can be variably aligned. Further indicators (e.g., a haptic feedback component, an audio feedback component, or the like) can be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; and U.S. patent application Ser. No. 14/173,266, filed Feb. 5, 2014, to Sears et al.; which are incorporated herein by reference.

A cartridge 104 can be formed of a cartridge shell 103 enclosing the reservoir 144 that is in fluid communication with a liquid transport element 136 adapted to wick or otherwise transport an aerosol precursor composition stored in the reservoir housing to a heater 134. Various embodiments of materials configured to produce heat when electrical current is applied therethrough may be employed to form the resistive heating element 134. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns) and ceramics (e.g., positive or negative temperature coefficient ceramics).

An opening 128 may be present in the cartridge shell 103 (e.g., at the mouthend) to allow for egress of formed aerosol from the cartridge 104. Such components are representative of the components that may be present in a cartridge and are not intended to limit the scope of cartridge components that are encompassed by the present disclosure.

The cartridge 104 also may include one or more electronic components 150, which may include an integrated circuit, a memory component, a sensor, or the like. The electronic component 150 may be adapted to communicate with the control component 106 and/or with an external device by wired or wireless means. The electronic component 150 may be positioned anywhere within the cartridge 104 or its base 140.

Although the control component 106 and the flow sensor 108 are illustrated separately, it is understood that the control component and the flow sensor may be combined as an electronic circuit board with the air flow sensor attached directly thereto. Further, the electronic circuit board may be positioned horizontally relative the illustration of FIG. 1 in that the electronic circuit board can be lengthwise parallel to the central axis of the control body. In some embodiments, the air flow sensor may comprise its own circuit board or other base element to which it can be attached. In some embodiments, a flexible circuit board may be utilized. A flexible circuit board may be configured into a variety of shapes, include substantially tubular shapes.

The control body 102 and the cartridge 104 may include components adapted to facilitate a fluid engagement therebetween. As illustrated in FIG. 1, the control body 102 can include a coupler 124 having a cavity 125 therein. The cartridge 104 can include a base 140 adapted to engage the coupler 124 and can include a projection 141 adapted to fit within the cavity 125. Such engagement can facilitate a stable connection between the control body 102 and the cartridge 104 as well as establish an electrical connection between the battery 110 and control component 106 in the control body and the heater 134 in the cartridge. Further, the control body shell 101 can include an air intake 118, which may be a notch in the shell where it connects to the coupler 124 that allows for passage of ambient air around the coupler and into the shell where it then passes through the cavity 125 of the coupler and into the cartridge through the projection 141.

A coupler and a base useful according to the present disclosure are described in U.S. Pat. Pub. No. 2014/0261495 to Novak et al., the disclosure of which is incorporated herein by reference in its entirety. For example, a coupler as seen in FIG. 1 may define an outer periphery 126 configured to mate with an inner periphery 142 of the base 140. In one embodiment the inner periphery of the base may define a radius that is substantially equal to, or slightly greater than, a radius of the outer periphery of the coupler. Further, the coupler 124 may define one or more protrusions 129 at the outer periphery 126 configured to engage one or more recesses 178 defined at the inner periphery of the base. Such protrusions and recesses may interact to function substantially as an anti-rotation mechanism so that the control body 102 and cartridge 104 remain positionally aligned. However, various other embodiments of structures, shapes, and components may be employed to couple the base to the coupler. In some embodiments the connection between the base 140 of the cartridge 104 and the coupler 124 of the control body 102 may be substantially permanent, whereas in other embodiments the connection therebetween may be releasable such that, for example, the control body may be reused with one or more additional cartridges that may be disposable and/or refillable.

The aerosol delivery device 100 may be substantially rod-like or substantially tubular shaped or substantially cylindrically shaped in some embodiments. In other embodiments, further shapes and dimensions are encompassed—e.g., a rectangular or triangular cross-section, multifaceted shapes, or the like.

The reservoir 144 illustrated in FIG. 1 can be a container or can be a fibrous reservoir, as presently described. For example, the reservoir 144 can comprise one or more layers of nonwoven fibers substantially formed into the shape of a tube encircling the interior of the cartridge shell 103, in this embodiment. An aerosol precursor composition can be retained in the reservoir 144. Liquid components, for example, can be sorptively retained by the reservoir 144. The reservoir 144 can be in fluid connection with a liquid transport element 136. The liquid transport element 136 can transport the aerosol precursor composition stored in the reservoir 144 via capillary action to the heating element 134 that is in the form of a metal wire coil in this embodiment. As such, the heating element 134 is in a heating arrangement with the liquid transport element 136.

In use, when a user draws on the article 100, airflow is detected by the sensor 108, the heating element 134 is activated, and the components for the aerosol precursor composition are vaporized by the heating element 134. Drawing upon the mouthend of the article 100 causes ambient air to enter the air intake 118 and pass through the cavity 125 in the coupler 124 and the central opening in the projection 141 of the base 140. In the cartridge 104, the drawn air combines with the formed vapor to form an aerosol. The aerosol is whisked, aspirated, or otherwise drawn away from the heating element 134 and out the mouth opening 128 in the mouthend of the article 100.

An input element may be included with the aerosol delivery device. The input may be included to allow a user to control functions of the device and/or for output of information to a user. Any component or combination of components may be utilized as an input for controlling the function of the device. For example, one or more pushbuttons may be used as described in U.S. patent application Ser. No. 14/193,961, filed Feb. 28, 2014, to Worm et al., which is incorporated herein by reference. Likewise, a touchscreen may be used as described in U.S. patent application Ser. No. 14/643,626, filed Mar. 10, 2015, to Sears et al., which is incorporated herein by reference. As a further example, components adapted for gesture recognition based on specified movements of the aerosol delivery device may be used as an input. See U.S. patent application Ser. No. 14/565,137, filed Dec. 9, 2014, to Henry et al., which is incorporated herein by reference.

In some embodiments, an input may comprise a computer or computing device, such as a smartphone or tablet. In particular, the aerosol delivery device may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. patent application Ser. No. 14/327,776, filed Jul. 10, 2014, to Ampolini et al., the disclosure of which is incorporated herein by reference. In such embodiments, an APP or other computer program may be used in connection with a computer or other computing device to input control instructions to the aerosol delivery device, such control instructions including, for example, the ability to form an aerosol of specific composition by choosing the nicotine content and/or content of further flavors to be included.

The various components of an aerosol delivery device according to the present disclosure can be chosen from components described in the art and commercially available. Examples of batteries that can be used according to the disclosure are described in U.S. Pat. Pub. No. 2010/0028766 to Peckerar et al., the disclosure of which is incorporated herein by reference in its entirety.

The aerosol delivery device can incorporate a sensor or detector for control of supply of electric power to the heat generation element when aerosol generation is desired (e.g., upon draw during use). As such, for example, there is provided a manner or method for turning off the power supply to the heat generation element when the aerosol delivery device is not be drawn upon during use, and for turning on the power supply to actuate or trigger the generation of heat by the heat generation element during draw. Additional representative types of sensing or detection mechanisms, structure and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference.

The aerosol delivery device most preferably incorporates a control mechanism for controlling the amount of electric power to the heat generation element during draw. Representative types of electronic components, structure and configuration thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. Pub. Nos. 2009/0230117 to Fernando et al., 2014/0060554 to Collet et al., and 2014/0270727 to Ampolini et al.; and U.S. patent application Ser. No. 14/209,191, filed Mar. 13, 2014, to Henry et al.; which are incorporated herein by reference.

Representative types of substrates, reservoirs or other components for supporting the aerosol precursor are described in U.S. Pat. No. 8,528,569 to Newton; U.S. Pat. Pub. Nos. 2014/0261487 to Chapman et al. and 2014/0059780 to Davis et al.; and U.S. patent application Ser. No. 14/170,838, filed Feb. 3, 2014, to Bless et al.; which are incorporated herein by reference. Additionally, various wicking materials, and the configuration and operation of those wicking materials within certain types of electronic cigarettes, are set forth in U.S. Pat. No. 8,910,640 to Sears et al.; which is incorporated herein by reference.

For aerosol delivery systems that are characterized as electronic cigarettes, the aerosol precursor composition most preferably incorporates tobacco or components derived from tobacco. In one regard, the tobacco may be provided as parts or pieces of tobacco, such as finely ground, milled or powdered tobacco lamina. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

The aerosol precursor composition, also referred to as a vapor precursor composition, may comprise a variety of components including, by way of example, a polyhydric alcohol (e.g., glycerin, propylene glycol, or a mixture thereof), nicotine, tobacco, tobacco extract, and/or flavorants. Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU™ product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. Typically, the amount of aerosol precursor incorporated within the aerosol delivery system, and particularly within the aerosol generating piece, is less than about 2 g, generally less than about 1.5 g, often less than about 1 g and frequently less than about 0.5 g.

Yet other features, controls or components that can be incorporated into aerosol delivery systems of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference.

The foregoing description of use of the article can be applied to the various embodiments described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article illustrated in FIG. 1 or as otherwise described above may be included in an aerosol delivery device according to the present disclosure.

In some embodiments, the present disclosure can relate to a power unit that is suitable for use in an aerosol delivery device. The power unit can comprise an elongated shell, and the shell particularly may be substantially tubular so as to define a cavity within the shell. The shell can have a proximal end and an opposing, distal end.

The elongated shell particularly can be characterized in relation to its separable nature. More specifically, the shell can be divided into two separate halves along a longitudinal axis thereof. In other words, the shell may be substantially cross-sectioned through the axis extending from the proximal end to the distal end. Although the separable portions of the shell may be referred to as "halves" throughout this disclosure, it is understood that such reference is not intended to limit the relatives sizes of the separable portions. In some embodiments, the separable halves (or separable portions) of the shell may be substantially equal in relation to the distance around the outer (or inner) surface of the shell. For example, FIG. 2 illustrates an embodiment wherein the halves are substantially equal in dimension such that each separable half (or separable portion) of the shell may form approximately 50% of the circumference of the shell. As seen therein, the shell 201 is separated substantially through the middle of the cross-section thereof so as to form a first half (portion) 2201a and a second half (portion) 2201b that are each approximately 50% of the circumference of the shell when the halves are combined. Further seen in the cross-section are a battery 210 and a battery lead 233, as further described below. While it may be useful for the two halves to be substantially equal in dimension, other embodiments are encompassed wherein the shell 201 is separated therethrough at a point other than the middle of the cross-section. The relative dimensions can be such that either half (portion) of the shell may be the larger portion.

In some embodiments, a construction wherein the shell is divided into separable portions may be referred to as a clam-shell structure. As such, the two separate halves of the shell may be substantially hinged together along at least a portion of the length of the shell. As illustrated in FIG. 3, for example, the shell 301 may be formed of a first half 301a that is hingedly attached to a second half 301b with a connecting member 315. The connecting member 315 may be formed of the same material as the shell 301 and may be a thinned or scored portion of the shell. In other embodiments, the two separate halves of the shell may be completely detached from each other but be configured to be attached to each other to form the completed power unit. In some embodiments, seams formed where the two halves connect may be sealed, such as through use of a sealant or by treating the shell (e.g., welding at the seams). Further seen in the cross-section are a battery 310 and a battery lead 333, as further described below.

In some embodiments, the two halves of the elongated shell used to form the power unit can be separably joined together. As such, the halves may be configured for being repeatedly attached and detached without any expected damage to the shell. For example, the two halves may include elements suited to form a snap-fit between the halves.

In further embodiments, the two halves of the elongated shell can be substantially permanently joined together. By such is meant that the two halves of the shell, one combined to form the completed shell, may not be physically separated by non-destructive actions. For example, the two halves of the shell may be welded together, glued together, or the like.

The structure of the shell (i.e., being provided as separate halves) can facilitate ease of assembling of the completed power unit. In conventional aerosol forming articles utilizing a substantially tubular shell, the shell is pre-formed in its completed state, and the internal components (e.g., batteries, electronics, electrical connections, etc.) are inserted into the completed shell from either end of the shell. As such, the internal components must be substantially completely connected prior to insertion. In other words, wires and the like used for forming electrical connections between a battery and a PCB, sensor, and/or a connector element must be soldered to the respective elements prior to insertion of the elements into the shell.

A power unit according to the present disclosure can thus solve the problem of ease of manufacture of a power unit, including ease of automation of the manufacture of the power unit. As will be further described below, a half (or portion) of the shell may be provided, and the various internal elements of the power unit may be laid into the partial shell. This can eliminate the need for soldering of elements in some embodiments, as otherwise described herein. Once the desired elements are laid into the partial shell, the remaining portion of the shell may be attached to form the completed shell with the power unit elements installed therein.

In like manner, the present construction can also facilitate ease of recycling of the various elements of the power unit. In conventional power units for aerosol forming devices, the entire unit must be discarded as a single piece after use of the device. While it is desirable to recycle the various elements of the power unit separately, the nature of the construction of conventional devices (e.g., all elements soldered together and inserted from an end into the non-separable shell) can prevent such recycling or significantly increase the difficulty of recycling.

According to the present disclosure, however, a used power unit may be easily de-constructed by simply separating the two halves of the shell. Although such separation may require cutting of at least a portion of the shell to free the two halves from one another, once one of the halves is removed, the individual elements within the shell may be easily removed for recycling, particularly in embodiments as described herein wherein the elements may be combined without the requirement of fusing (e.g., soldering).

A shell according to the present disclosure may be formed of a variety of materials. In some embodiments, plastic materials may be used, such as high density polyethylene terephthalate (HDPE), polypropylene, polycarbonate, or the like. In further embodiments, metal materials may be used, such as aluminum or steel. In specific embodiments, the shell may be substantially a plastic clam-shell.

Many of the elements included in a power unit as described herein may be present in previously known power units. As will be seen below, however, the various elements may be provided in different forms in light of the ease of manufacture of the present device.

In some embodiments, a power unit according to the present disclosure can comprise at least one elongated battery positioned within the elongated shell. The at least one battery can be characterized as extending from the distal end of the second elongated shell toward the proximal end of the elongated shell. In other words, the at least one battery may be positioned closer to the distal end (particularly adjacent the distal end) of the shell than to the proximal end of the shell. In particular embodiments, a single battery may be used or two batteries may be used. The total number of batteries that are utilized can depend upon the rated capacities of the batteries that are used (e.g., the voltage rating of the battery).

Such configuration is illustrated in FIG. 4, wherein a power unit 401 is formed of a first shell half 4201a and a second shell half 4201b which, when combined to form the completed shell 4201, enclose a battery 410 and a battery lead 433. The battery 410 comprises a positive terminal 410a and a negative terminal 410b. In embodiments where two batteries, for example, may be utilized, the batteries may be aligned in electrical series such that the negative terminal of the first battery is substantially adjacent the distal end 4301b of the power unit shell 4201, and the positive terminal of the second battery is substantially adjacent the proximal end 4301a of the power unit shell 4201.

The power unit 401 further comprises a battery lead 433 that is configured for forming electrical connections of the various components of the aerosol delivery device to the battery 410. As illustrated, the battery lead 433 includes a projection 433b that is configured for electrical connection with a terminal of the battery 410. In the illustrated embodiment, the projection 433b is configured for electrical connection with the negative terminal 410b. The projection is illustrated to be substantially round; however, other configurations are also encompassed. A biasing member 445 may be included to bias the projection 433b toward the terminal 410b of the battery 410. In the illustrated embodiment, the biasing member 445 is a spring; however, further embodiments are also encompassed. The biasing member 445 may particularly be configured for contacting the end cap 411 of the power unit 401. Said end cap 411 can be attached to one or both of the first shell half 4201a and the second shell half 4201b, such as by crimping, welding, gluing, or the like, and the end cap may be made of any material, including metals and plastics. The end cap 411 may be transparent or translucent if desired and may, for example, allow external visibility of a light source that may be included in the power unit 401. See, for example, element 112 in FIG. 1. In such embodiments, the biasing member 445 may attach, for example, to one or both of the first shell half 4201a and the second shell half 4201b. In some embodiments, the end cap 411 may be substantially captured between the clam shell hales 4201a and 4201b.

The battery lead 433 further includes an arm 433a extending from the projection 433b along the length of the battery 410. The aim 433a can be configured to provide electrical connection with one or more further elements of the power unit 401, or a further component of an aerosol delivery device. The battery lead 433 can be formed of any electrically conductive materials, particularly metals, such as copper. Beneficially, the battery lead 433 can be configured for forming electrical connections with the battery and one or more further elements of the aerosol delivery device without the requirement of soldering or other means for fusing electrical connections.

A power unit 401 can, in some embodiments, further comprise a base unit 424 attached at the proximal end 4301a of the shell 4201. As will be evident from the further disclosure provided herein, the base unit 424 can be an element of a completed power unit 401, can be an element of a completed cartridge (see element 104 of FIG. 1), or can be a separate element of an aerosol delivery device (see 100 in FIG. 1) that may, for example, interconnect a power unit to a cartridge.

The base unit 424 can include a first base section 424a that has a first diameter and a second base section 424b that has a second diameter that is less than the first diameter. The first diameter can be substantially similar to the diameter of the shell 4201 of the power unit 401. In particular, the first diameter of the first base section 424a can be substantially identical to the inner diameter of the shell 4201 so that the shell may be attached to the first base section. The first base section 424a may include a first heater terminal opening 427a and a second heater terminal opening 427b that provide access for heater terminals to pass into the base unit 424 for connection to a control and/or power member, as further discussed below. The first and second heater terminal openings, as illustrated, are positioned in a wall 4424a defining the first section of the base unit. The first base section 424a further can include an air intake 418 through which air may be drawn during use of a completed aerosol delivery device. The air intake 418, as illustrated, is positioned in a skirt 4424a' extending longitudinally from the wall so as to further define the first section 424a of the base unit 424. The wall 4424a and the skirt 4424a' of the first section 424a of the base unit 424 may intersect at a substantially right angle (although other angular arrangements are also encompassed). The base unit 424 may include a cavity 425 that extends at least partially therethrough. For example, the cavity 425 may extend at least from the air intake 418 through an open end of the second base section 424*b*. As further described herein, the second base section 424*b* may connect with a portion of a cartridge so that air drawn through the air intake 418 passes through the intake, through the cavity 425, through the second base section 424*b*, and into the cartridge for combining with formed vapor. The second base section 424*b* can be formed of a longitudinal wall 4424*b* extending from the wall 4424*a* of the first base section 424*a* and may be substantially parallel with the skirt 4424*a*' of the first base section. The skirt may include anti-rotational elements (see FIG. 1).

As noted previously, an aerosol delivery device may include one or both of a control component and a pressure sensor. In some embodiments, the base unit can include one or both of the control component and a pressure sensor. For example, a PCB may be mounted to (or otherwise combined with) the base unit. In some embodiments, the PCB may be at least partially interior to the base unit.

One embodiment of a base unit 524 is illustrated in FIG. 5*a*, which shows the distal end 5524*a* of the base unit. A PCB 5106 is positioned at the distal end 5524*a* of the base unit 524 and can include the circuitry necessary to provide control functions to an aerosol delivery device in which it is incorporated. The PCB 5106 particularly can be interior to the skirt 5424*a*' of the first base section 524*a*. The PCB 5106 can include a sensor 5108. As illustrated, the sensor 5108 is positioned on the opposing side of the PCB 5106 so as to be in proximity to the air intake 418. In some embodiments, a support plate 537 may be present and may substantially or completely separate the PCB 5106 from the cavity 525 in the base unit 524. The support plate 537 may form a liquid impermeable or air-tight relationship with the base unit 524 so that liquid from a cartridge may not pass therethrough into a power unit and/or so that air does not pass through or from a power unit prior to being drawn into a cartridge. The sensor 5108 may pass through the support plate 537 so as to be at least partially positioned within the cavity 525 of the base unit 524.

The PCB 5106 can include a plurality of electrical contacts. As the PCB 5106 can be combined with the base unit 524, in some embodiments, the base unit can be characterized as including a plurality of electrical contacts. In the example of FIG. 5*a*, the PCB 5106 includes a first battery contact 5106*c* that can be configured for electrical connection with the positive terminal 410*a* of the battery 410. The first battery contact 5106*c* may protrude from the PCB 5106*a* sufficient distance to bridge any open space between the base unit 524 and the battery 410. The PCB 5106 further includes a first heater contact 5106*a* and a second heater contact 5106*b* configured for electrical connection with first and second heater terminals, respectively, that may pass through the first heater terminal opening 527*a* and the second heater terminal opening 527*b* in the base unit 524.

The base unit 524 further can include a second battery contact 531, which may be positioned on the base unit so as to be in contact with a corresponding contact on the PCB 5106. Alternatively, the second battery contact 531 may be positioned on the PCB 5106, which is itself attached to the base unit 524. As illustrated in FIG. 5*a*, the second battery contact 531 is connected to the first base section 524*a* of the base unit 524, and the PCB 5106 is in electrical connection therewith. The second battery contact 531 can be configured for electrical connection with the negative terminal 410*b* of the battery 410. Electrical connection between the second battery contact 531 and the negative terminal 410*b* of the battery 410 may be via the battery lead 433. The second battery contact 531 may be sufficiently sized to ensure contact with the battery lead 433 through a variety of positions. In some embodiments, the second battery contact 531 may be shaped to receive a portion of the battery lead 433. For example, the second battery contact 531 may be substantially tubular, and the battery lead 433 may slide into the tubular portion of the second battery contact to maintain electrical connection. Alternatively, a clip may be used to interconnect the second battery contact 531 and the battery lead 433. Such configurations can allow for the electrical connection between the second battery contact 531 and the battery lead 433 to be non-fused—i.e., not requiring solder to form or secure the connection.

The proximal end 5524*b* of the base unit 524 is visible in FIG. 5*b*. As seen therein, the cavity 525 extends through the second base section 524*b* such that the support plate 537 is visible. Likewise, the first heater contact 5106*a* and the second heater contact 5106*b* are visible through the first heater terminal opening 527*a* and the second heater terminal opening 527*b*, respectively, in the wall 5424*a* of the first base section 524*a*.

A power unit, separately or in combination with a base unit, can be utilized in forming an aerosol delivery device. In particular, the power unit can be combined with a cartridge that includes an atomizer and that is configured for receiving and storing an aerosol forming composition. Even more particularly, the cartridge can be configured for attachment to the proximal end of the base unit so that the power unit, the base unit, and the cartridge together form the aerosol delivery device. A cartridge that can be configured for combination with a power unit and/or base unit as described herein is described in U.S. patent application Ser. No. 14/286,552, filed May 23, 2014, to Brinkley et al., the disclosure of which is incorporated herein by reference.

An example embodiment of a cartridge 604 configured for combination with a power unit is shown in FIG. 6. As seen therein, the cartridge 604 comprises an elongated shell 603 with a reservoir 644 therein. The reservoir 644 may be, for example, a fibrous mat (e.g., cellulose acetate), although other types of reservoirs (e.g., containers) are also encompassed. A liquid transport element 636 can be combined with a heater 634 to form an atomizer. The liquid transport element 636 can particularly extend at least partially through the reservoir 644 in the exemplified embodiment. The heater 634 can be positioned near a midpoint of the liquid transport element 636. For example, the heater 634 may be a resistive heating wire wrapped around the liquid transport element 636. The heater-wrapped portion of the liquid transport element 636 may extend out of one end of the reservoir 644, particularly an end of the reservoir near a proximal end 603*a* of the cartridge shell 603. A mouthpiece 647 may be combined with the cartridge shell 603 at the proximal end 603*a* thereof. The proximal end 603*a* of the cartridge shell 603 may be characterized as the mouth end, and the distal end 603*b* of the cartridge shell may be characterized as the joining end of the shell. The joining end of the cartridge shell and the proximal end 4301*a* may be configured for connection together.

The base unit 524 may be configured for connection with the power unit shell 4201. The base unit 524 may be configured for connection with the cartridge shell 603. The base unit 524 may be configured for connection with both the power unit shell 4201 and the cartridge shell 603.

The cartridge 604 further can include an elongated flow tube 648 that can be configured for directing air flow through the cartridge. In particular, the flow tube 648 can include a central airflow passage 648*a* extending therethrough. The flow tube 648 further can be configured for physical connection with the base unit 524, electrical connection with the base unit, or both physical and electrical connection with the base unit.

In some embodiments, the proximal end 5524b of the second base section 524b can be configured to engage the flow tube 648, such as through at least partial insertion into the central airflow passage 648a. With such physical connection, when drawing on the mouthpiece 647 of the cartridge 604, air can enter the air intake 418 of the base unit 424, pass through the cavity 425, enter the central airflow passage 648a of the flow tube 648, pass across the heater 634 in combination with the liquid transport element 636, and exit through the mouthpiece.

The flow tube 648 includes a first heater terminal 649a and a second heater terminal 649b, and such terminals particularly may be configured for establishing an electrical connection between the cartridge and the base unit 524. For example, ends of the heater terminals extending from the end of the flow tube 648 near the distal end 603b of the cartridge shell 603 may be configured for insertion into the first heater terminal 527a and the second heater terminal 527b for making electrical connection with the first heater contact 5106a and the second heater contact 5106b of the PCB 5106. As such, the heater terminals can be configured for electrical connection with the base unit 524. The heater terminals (527a, 527b) may be characterized as extending through the flow tube 648. In the illustrated embodiment, the heater terminals (527a, 527b) are integrated with the flow tube 648 and extend through a flange 675 of the flow tube.

Formation of an aerosol delivery device can include attaching the base unit to one of the power unit shell and the cartridge shell and then attaching the other of the power unit shell and the cartridge shell thereto. In some embodiments, the base unit can be attached to the flow tube of the cartridge, and this combination can be combined with the power unit prior to connecting the first and second halves of the power unit shell. In this manner, the second battery contact on the base unit can be positioned in electrical connection with the battery lead. The two halves of the power unit shell may then be interconnected. Such connection may provide a substantially tight fit with the cartridge shell such that no further holding means are required. Further, a label may be placed around the aerosol delivery device, and the presence of the label may further maintain the interconnection of the power unit shell and the cartridge shell. In some embodiments, gluing, welding, crimping, or the like may be used in interconnecting the power unit shell and the cartridge shell.

In some embodiments, a method for forming an aerosol delivery device can comprise providing the first shell half of the power unit shell. As discussed above the first shell half can be configured for attachment to the second shell half to form the elongated clam shell that is the power unit shell. As such, the power unit clam shell can be characterized as being divided into a first half and a second half along a longitudinal axis thereof. The assembly method further can comprise placing the battery lead and the battery (or plurality of batteries) into the first shell half. This placement can be such that the projection of the battery lead is in electrical connection with a first terminal of the battery and such that the arm of the battery lead extends from the projection along the length of the battery. In particular, the battery lead projection can be configured to be in electrical connection with the negative terminal of the battery, and the arm of the battery lead can be configured to be in electrical connection with the positive terminal of the battery (include the use of one or more interconnecting elements, such as the battery contact on the base unit). The assembly method further can comprise providing the base unit that can include various elements as discussed above. For example, the base unit can comprise a PCB, a pressure sensor, a first battery contact configured for electrical connection with the positive terminal of battery and a second battery contact configured for electrical connection with the arm of the battery lead. The first battery contact can be part of the PCB, and the second battery contact can be attached to the base unit, attached to the PCB, or attached to both the base unit and the PCB. The assembly method further can comprise providing a cartridge as described herein. For example, the cartridge can comprise a shell that houses: a reservoir for an aerosol-forming composition; a heater; a liquid transport element configured for transport of the aerosol forming composition between the reservoir and the heater; and heater terminals. The assembly method further can comprise combining the cartridge, the base unit, and the first shell half such that the heater terminals are in electrical connection with the base unit, the first battery contact of the base unit is in electrical connection with the second terminal (the positive terminal in this example) of the battery, and the second battery contact of the base unit is in electrical connection with the arm of the battery lead (which ultimately provides electrical connection with the negative terminal of the battery. The assembly method further can comprise pairing the second shell half to the first shell half. As noted above, the interconnection of the power unit shell, the cartridge shell, and the base unit can include one or more of crimping, laser welding, and gluing the clam shell to one or both of the base unit and the cartridge shell.

In addition to the foregoing, the present disclosure encompasses alternative configurations whereby electrical connection can be provided between a heater and a power unit. Such configurations can include, for example, modifications to one or both of a flow tube and a base unit as otherwise described herein. The configurations specifically can relate to a removable attachment of a cartridge and a control body. As such, the control body may be reusable (i.e., including a rechargeable battery and charging elements). The configurations further specifically can relate to securing a non-removable attachment of a cartridge and a control body.

In an embodiment as illustrated in FIGS. 7a and 7b, heater terminals 749a and 749b can be configured for a transverse sliding arrangement with the base unit 724 so as to provide a substantially permanent engagement therebetween in combination with a power unit housing. In particular, a base unit 724 can include a PCB 7106 with a sensor 7108, a first battery contact 7106c, and a second battery contact 731. The base unit 724 can be configured to engage a flow tube 748 of a cartridge unit (see FIG. 6), which flow tube can include a first heater terminal 749a and a second heater terminal 749b that are substantially L-shaped (i.e., include an extension that is substantially parallel to the longitudinal axis of the flow tube and a projection that is substantially perpendicular to the longitudinal axis of the flow tube), although other similar structures are also encompassed. In assembly, the first and second heater terminals (749a and 749b) slide around the perimeter of the base unit 724 such that the projections on the heater terminals are positioned under the base unit and the extensions of the heater terminals are along the side of the base unit. In this manner, the base unit is substantially cradled by the flow tube 748 and the heater terminals (749a and 749b), and the flow tube cannot be disengaged from the base unit via longitudinal movement. Once the combined flow tube 748 and base unit 724 are positioned within the power unit shell (see element 4201 in FIG. 4), the sliding relationship is no longer possible, and a substantially permanent attachment is provided. In this configuration, the first heater terminal 749a is in electrical connection with the first heater contact 7106a of the PCB 7106, and the second heater terminal 749b is in electrical connection with the second heater contact 7106b of the PCB. The construct further can include an insulator cap 781 that substantially covers the sensor 7108 to prevent electrical shorting. The insulator cap 781 can include an aperture 788 to provide fluid access to the sensor.

In an embodiment as illustrated in FIGS. 8a and 8b, heater terminals 849a and 849b can be configured for a longitudinal engagement with heater contacts 8106a and 8106b of the base unit 824 so as to provide a substantially removable engagement therebetween. In particular, a base unit 824 can include a PCB 8106 with a sensor 8108, a first battery contact 8106c, and a second battery contact 831. The base unit 824 can be configured to engage a flow tube 848 of a cartridge unit (see FIG. 6), which flow tube can include a first heater terminal 849a and a second heater terminal 849b that extend therefrom. In assembly, the first and second heater terminals (849a and 849b) make a "wiping" connection with the first and second heater contacts (8106a and 8106b), which extend upward from the base unit 824. The first and second heater terminals 849a and 849b) and or the first and second heater contacts (8106a and 8106b) can flex (i.e., exhibit a spring characteristic) so that a heater terminal and a heater contact are biased together when making the wiping connection. As illustrated, the heater terminals and heater contacts include shaped sections to better facilitate contact therebetween in making an electrical connection. In this manner, the base unit 824 and the flow tube 848 may exhibit a substantially longitudinal press-fit whereby the engagement of the heater terminals and heater contacts participates in the structural connection therebetween. So as to enclose the space between the flow tube 848 and the base unit 824 wherein the heater terminals and heater contacts make the wiping connection, a middle housing 880 may be included, and may be formed of an outer wall 881 and an inner plate 882 (as seen in the partial cross-section of the middle housing illustrated in FIG. 8a). With such construction, an annular gap 883 provides space for the wiping connection to occur, and the middle housing can function to substantially prevent electrical shorting. The middle housing 880 may be permanently or removably connected to one of the base unit 824 and the flow tube 848 so as to prevent loss of the piece when the flow tube and the base unit are not connected. In particular embodiments wherein the power unit that includes the base unit 824 is a reusable component and the cartridge that includes the flow tube 848 is a disposable component, the middle housing 880 may particularly be permanently engaged with the base unit. In other embodiments, the middle housing 880 may be permanently or removably engaged with a power unit shell or a cartridge shell.

Although the foregoing disclosure may describe embodiments of an aerosol delivery device (or power unit thereof) in relation to the use of a clam-shell structure, it is understood that the further components of the device may be utilized with a single piece shell (i.e., a tube that is not longitudinally separable). Accordingly, in some embodiments, the present disclosure relates to a "drop-in" construct wherein a tube may be provided as the power unit shell (i.e., in place of the first shell half 4201a and the second shell half 4201b in FIG. 4). In particular, the single piece shell can be provided (including an end cap), and the biasing member 445, the battery lead 433, and the battery 410 may be sequentially dropped into the shell. Thereafter, the base unit 424 may be added. If desired, the base unit may be connected to a cartridge (e.g., to a flow tube, such as discussed above in relation to FIG. 8a and FIG. 8b) prior to being added to the power unit shell. Any of the embodiments described above may be utilized as appropriate with a single piece tube in this manner.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device comprising:
   a first elongated shell having a mouth end and an opposing joining end, the first elongated shell housing:
      a reservoir for an aerosol-forming composition;
      a heater;
      a liquid transport element configured for transport of the aerosol forming composition between the reservoir and the heater; and
      heater terminals;
   a second elongated shell having a proximal end configured for connection with the joining end of the first elongated shell and having an opposing, distal end, the second elongated shell being divided into two separate halves along a longitudinal axis thereof;
   at least one battery positioned within the second elongated shell; and
   a base unit defined by at least one wall and having an open interior, the base unit comprising:
      a printed circuit board (PCB) positioned at least partially within the open interior, the printed circuit board including a first contact configured for electrical connection with a terminal of the at least one battery, a second contact configured for electrical connection with an opposing terminal of the at least one battery, and first and second heater contacts configured for electrical connection with the heater terminals.

2. The aerosol delivery device according to claim 1, wherein the two halves of the second elongated shell are separably joined together.

3. The aerosol delivery device according to claim 1, wherein the two halves of the second elongated shell are permanently joined together.

4. The aerosol delivery device according to claim 1, wherein the two halves of the second elongated shell are welded together.

5. The aerosol delivery device according to claim 1, wherein the base unit comprises a pressure sensor.

6. The aerosol delivery device according to claim 1, further comprising a battery lead positioned within the second elongated shell, the battery lead including a projection that is configured for electrical connection with the opposing terminal of the at least one battery and including an arm extending from the projection along the length of the at least one battery so as to be in electrical connection with the second contact of the printed circuit board positioned at least partially within the open interior of the base unit.

7. The aerosol delivery device according to claim 6, wherein the electrical connections with the terminal and opposing terminal of the battery are non-fused.

8. The aerosol delivery device according to claim 1, wherein the aerosol delivery device comprises an elongated flow tube positioned at least partially within the first elongated shell, the elongated flow tube comprising a central airflow passage therethrough.

9. The aerosol delivery device according to claim 8, wherein the elongated flow tube is configured for one or both of physical and electrical connection with the base unit.

10. The aerosol delivery device according to claim 9, wherein the heater terminals pass through the flow tube and include ends that make the electrical connection with the first and second heater contacts on the printed circuit board positioned at least partially within the open interior of the base unit.

11. The aerosol delivery device according to claim 1, wherein the aerosol delivery device comprises a mouthpiece attached to the mouth end of the first elongated shell.

12. The aerosol delivery device according to claim 1, wherein the flow tube is attached to the base unit.

13. The aerosol delivery device according to claim 1, wherein the joining end of the first elongated shell is connected to at least a portion of the base unit.

14. The aerosol delivery device according to claim 1, wherein the proximal end of the second elongated shell is connected to at least a portion of the base unit.

15. The aerosol delivery device according to claim 1, wherein the base unit comprises a first base section that has a first diameter and a second base section that has a second diameter that is less than the first diameter.

16. The aerosol delivery device according to claim 15, wherein the first diameter of the first base section is substantially similar to an inner diameter of the shell second elongated shell.

17. The aerosol delivery device according to claim 15, wherein the first base section includes at least one heater terminal opening through which the heater terminals pass into the base unit.

18. The aerosol delivery device according to claim 15, wherein the first base section includes an air intake.

19. A method for forming an aerosol delivery device comprising:
providing a first longitudinal half shell that is configured for attachment to a second longitudinal half shell to form an elongated clam shell that is divided into a first half and a second half along a longitudinal axis thereof;
placing a battery lead and at least one battery into the first longitudinal half shell such that a projection of the battery lead is in electrical connection with a first terminal of the at least one battery and such that an arm of the battery lead extends from the projection along the length of the at least one battery;
providing a base unit defined by at least one wall and having an open interior, the base unit comprising a printed circuit board (PCB) positioned at least partially within the open interior, the printed circuit board including a first contact configured for electrical connection with a terminal of the at least one battery, a second contact configured for electrical connection with an opposing terminal of the at least one battery, and first and second heater contacts configured for electrical connection with the heater terminals;
providing a cartridge comprising a shell:
a reservoir for an aerosol-forming composition:
a heater;
a liquid transport element configured for transport of the aerosol forming composition between the reservoir and the heater; and
heater terminals;
combining the cartridge, the base unit, and the first longitudinal half shell such that the heater terminals are in electrical connection with the first and second heater contacts on the PCB positioned at least partially within the open interior of the base unit, the first contact on the PCB is in electrical connection with the second terminal of the at least one battery, and the second contact on the PCB is in electrical connection with the arm of the battery lead; and
pairing the second longitudinal half shell to the first longitudinal half shell to form a completed power unit shell in physical connection with the base unit.

20. The method of claim 19, comprising first adding the base unit to the first longitudinal half shell and then attaching the cartridge to the base unit.

21. The method of claim 19, comprising first attaching the cartridge to the base unit and then adding the base unit to the first longitudinal half shell.

22. The method of claim 19, comprising one or more of crimping, welding, and gluing the clam shell to one or both of the base unit and the cartridge shell.

23. A power unit for an aerosol delivery device comprising:
an elongated shell having a proximal end and an opposing, distal end, the elongated shell being divided into two separate halves along a longitudinal axis thereof;
a battery positioned within the elongated shell, the battery extending from the distal end of the elongated shell toward the proximal end of the elongated shell; and
a base unit attached at the proximal end of the elongated shell, the base unit being defined by at least one wall and having an open interior.

24. The power unit according to claim 23, wherein the two halves of the elongated shell are separably joined together.

25. The power unit according to claim 23, wherein the two halves of the elongated shell are permanently joined together.

26. The power unit according to claim 23, wherein the two halves of the elongated shell are welded together.

27. The power unit according to claim 23, comprising a battery lead including a projection that is configured for electrical connection with a terminal of the at least one battery and including an arm extending from the projection along the length of the at least one battery.

28. The power unit according to claim 23, wherein the base unit comprises a printed circuit board (PCB) positioned at least partially within the open interior of the base unit.

29. The power unit according to claim 28, wherein the PCB includes a first contact configured for electrical connection with the terminal of the at least one battery and includes a second contact configured for electrical connection with an opposing terminal of the at least one battery.

30. The power unit according to claim 29, wherein the battery lead projection is configured for electrical connection with a negative terminal of the at least one battery, and the battery lead arm is configured for electrical connection with one of the first contact and the second contact of the base unit.

31. The power unit according to claim 30, wherein the electrical connections are non-fused.

* * * * *

UNITED STATES PATENT AND TRADEMARK OFFICE
CERTIFICATE OF CORRECTION

PATENT NO. : 11,000,069 B2
APPLICATION NO. : 14/713430
DATED : May 11, 2021
INVENTOR(S) : Ampolini et al.

It is certified that error appears in the above-identified patent and that said Letters Patent is hereby corrected as shown below:

On the Title Page

In the References cited, item (56) under Foreign Patent Documents section, Page 3, Column 2, Line 1, The foreign patent document number appears as:
"DE 10 2006 004 4"
And it should be corrected as follows:
"DE 10 2006 004 484"

In the Claims

Column 23, Lines 37-38:
"inner diameter of the shell second elongated shell"
Please correct Claim 16 to read as follows:
"inner diameter of the second elongated shell"

Signed and Sealed this
Twenty-third Day of August, 2022

Katherine Kelly Vidal
*Director of the United States Patent and Trademark Office*